United States Patent [19]
Frei

[11] Patent Number: 5,411,396
[45] Date of Patent: May 2, 1995

[54] METHOD OF AND IMPLEMENT FOR EXTRACTION OF DENTAL PROSTHESES

[75] Inventor: Siegfried Frei, Teufen, Switzerland

[73] Assignee: ATD S.A.R.L., Cedex, France

[21] Appl. No.: 188,086

[22] Filed: Jan. 28, 1994

[30] Foreign Application Priority Data

Jan. 28, 1993 [CH] Switzerland ............... 00246/93

[51] Int. Cl.⁶ ............................................. A61C 3/00
[52] U.S. Cl. ....................................... 433/153; 433/215
[58] Field of Search .................... 433/1, 153, 154, 157, 433/158, 159, 161, 215

[56] References Cited

U.S. PATENT DOCUMENTS

| | | | |
|---|---|---|---|
| 4,417,876 | 11/1983 | Lynch | 433/161 |
| 4,749,352 | 6/1988 | Nicholson | 433/9 |
| 5,197,877 | 3/1993 | Andrew | 433/153 |
| 5,197,878 | 3/1993 | Lukase et al. | 433/158 |

FOREIGN PATENT DOCUMENTS

| | | |
|---|---|---|
| 0471648 | 2/1992 | European Pat. Off. |
| 3525836C1 | 10/1986 | Germany . |
| 3808880A1 | 9/1989 | Germany . |

Primary Examiner—Cary E. O'Connor
Attorney, Agent, or Firm—Darby & Darby

[57] ABSTRACT

A prosthesis which is affixed to at least one tooth can be extracted from the mouth of a patient by an implement employing two discrete substantially disc-shaped jaws which are to be bonded to spaced-apart portions of the external surface of the prosthesis by a rapidly setting adhesive. The jaws are permanently or separably connected to spaced-apart portions of an endless cable or to the end portions of a cable of finite length, and the cable is engaged by a follower of a tool which is used by a dentist to pull the cable and to thus detach the prosthesis from the at least one tooth. The adhesive can be polymerizable in response to exposure to light (such as ultraviolet light) which is transmitted thereto through the jaws by an optical conductor. The jaws are deformed or can be deformed so that one side of each jaw, which confronts a portion of the external surface of the prosthesis to be extracted, has an outline at least substantially conforming to the outline of the respective portion of the external surface.

27 Claims, 3 Drawing Sheets

METHOD OF AND IMPLEMENT FOR EXTRACTION OF DENTAL PROSTHESES

BACKGROUND OF THE INVENTION

The present invention relates to improvements in implements, kits or apparatus (hereinafter called implements) for nondestructive extraction of dental prostheses (e.g., in the form of single crowns of plural crowns connected to each other by one or more bridges) from the mouth of a patient, i.e., for detachment of a prosthesis from a single tooth or from several teeth, without damage to or destruction of the prosthesis.

It is already known to separate dental prostheses from teeth (i.e., to break the bonds between the external surface of a tooth and the surrounding crown or to break the bonds between several crowns of a prosthesis and the respective teeth) by utilizing an implement having one or more relatively small hooks engageable with the edge surrounding the cavity of a crown adjacent the gums in a patient's mouth and to exert upon the hook or hooks a pull in a direction to lift the crown off the tooth. The means for exerting a pull can comprise a standard tool which includes a rod with a stop or anvil at one end and a weight or hammer which is slidable along the rod to repeatedly strike against the stop and to thus exert a pull upon the hook or hooks in a direction to terminate the bond between the crown and the respective tooth. A drawback of such implements is that the engagement of the edge of a crown by one or more hooks is often painful to the patient because the hook or hooks must displace the gums which are likely to bleed and to become infected. Moreover, the hooks engage a very thin portion of a crown, namely an edge having a thickness in the range of a minute fraction of one millimeter (e.g., approximately 0.2 mm) so that the hooks are likely to damage the edge of a crown in response to repeated impacts of the weight or hammer against a stop at one end of the rood which is coupled to a crown by one or more jaws. Detachment of a prosthesis (which can consist of a ceramic material or a metal-ceramic compound) from one or more teeth is necessary when the prosthesis is damaged or has undergone extensive wear as well as due to inflammation of the gums and/or damage to the material which bonds the prosthesis to one or more teeth. Any, even very slight, damage to a prosthesis during detachment from one or more teeth must be repaired by a skilled technician in a time-consuming operation. Therefore, the just described conventional mode of detaching dental prostheses from teeth is not satisfactory if the prosthesis is to be extracted without any damage to its crown or crowns. Another drawback of the aforedescribed conventional implements is that a hook which engages an edge of a crown exerts a pull against one side of the respective crown, i.e., the crown is detached in response to the application of a pull to one side of a crown; this is even more likely to entail damage to the prosthesis, discomfort to the patient and to necessitate the application of a relatively large force which is bound to result in deformation of the crown or crowns and in destruction of the compound which was used to bond a prosthesis to one or more teeth of a patient. Any damage to the bonding material necessitates a time-consuming repair work at a substantial cost or, in many cases, complete removal of bonding material and the making of a new prosthesis with one or more crowns and one or more bridges between neighboring crowns.

U.S. Pat. No. 5,197,877 (granted Mar. 30, 1993 to Andrew for "Implement For Extracting Dental Crowns, Bridges And The Like") discloses an implement wherein selected portions of the external surface of a crown can be engaged by two jaws which are biased against the crown during extraction of the crown (or of a prosthesis with several crowns and one or more bridges) by a tool utilizing an elongated rod and a reciprocable weight or hammer which is to strike an enlarged portion or anvil at one end of the rod. The implement of Andrew exhibits the advantage that the external surface of a crown can be engaged at spaced-apart locations so that the pull upon the crown during extraction is applied to spaced-apart portions of the crown. The surfaces of the jaws can be roughened to ensure reliable temporary engagement with selected portions of the external surface of a crown. Problems can arise if a particular crown cannot be engaged by two jaws with adequate friction so that the jaws are likely to slip relative to a crown during attempted extraction of a prosthesis from the mouth of a patient.

German Patent Application Serial No. 38 08 880 A1 of Schäfer et al. for "Apparatus For Removing Substitute Teeth" (published Sep. 28, 1989) discloses an implement wherein a bar carries one or more wire loops extending beneath one or more bridges of a composite prosthesis having at least two crowns and a bridge between them. Two adjustable pushers are provided to react against teeth which flank the multiple-crown prosthesis and to bear against the bar so that the bar exerts a pull upon the wire loop or loops which, in turn, lifts or lift the crowns off the respective teeth by exerting a pull upon the bridge or bridges. A drawback of such a proposal is that the implement cannot be utilized for removal of prostheses consisting of a single crown as well as that the implement can be used only if a multiple-crown prosthesis is flanked by two uncrowned teeth.

German Patent No. 35 25 836 C1 of Planert for "Apparatus For Engaging And Extracting Crowns, Bridges And The Like And/Or Portions Of Teeth" (granted Oct. 10, 1986) discloses an implement employing an u-shaped frame having legs which are to be bonded to two sides of a crown, and a web extending between the legs and provided with an eyelet which can be connected to a device serving to pull the frame in a direction to detach the crown from the corresponding tooth or stub of a tooth. A drawback of the apparatus of Planert is that a number of different frames must be supplied to a dentist in order to ensure that the dentist will be able to locate a frame which is best suited for bonding of its legs to the sides of a particular crown.

U.S. Pat. No. 4,749,352, granted Jun. 7, 1988 to Nicholson for "Method Of Bonding Orthodontic Brackets", discloses a bracket which is to be bonded to one side of a tooth by a rapidly setting adhesive. The adhesive is polymerized in response to the exposure to visible and/or ultraviolet light. The method of Nicholson is not intended and is not suitable for the extraction of prostheses. The disclosure of this patent is incorporated herein by reference.

OBJECTS OF THE INVENTION

An object of the invention is to provide a simple method of extracting prostheses from the mouths of patients in a time saving manner.

Another object of the invention is to provide a method which can be relied upon to extract one-crown or multiple-crown prostheses without any damage thereto.

A further object of the invention is to provide a method which renders it possible to extract prostheses in such a way that the pulling force is applied to several spaced-apart portions of a crown which is to be separated from a tooth or from a portion (stub) of a tooth.

An additional object of the invention is to provide a method which can be practiced by resorting to simple and inexpensive apparatus.

Still another object of the invention is to provide a method which renders it possible to avoid any slippage of the extracting implement relative to a prosthesis which is to be detached from one or more teeth or stubs.

A further object of the invention is to provide an implement or apparatus which can be utilized for the practice of the above outlined method and is constructed and can be operated in such a way that it does not affect the appearance and/or integrity of a prosthesis.

Another object of the invention is to provide an implement which can be used for extraction of single crowns or of multiple-crown prostheses and which need not contact the gums of a patient preparatory to or during extraction of a prosthesis.

An additional object of the invention is to provide the implement with novel and improved means for engaging a crown or one of several crowns forming part of a dental prosthesis.

Still another object of the invention is to provide the implement with novel and improved means for separably coupling the crown-contacting parts with a tool which is used to pull the crown off a tooth or tooth stub.

A further object of the invention is to provide a novel and improved method of separably attaching the above outlined implement to a dental prosthesis.

Another object of the invention is to provide an implement which can be utilized with equal facility for the extraction of large, small or medium-sized crowns and which can be readily separated from a detached prosthesis.

SUMMARY OF THE INVENTION

One feature of the present invention resides in the provision of a method of nondestructively extracting a dental prosthesis (such as a crown) of the type affixed to at least one tooth. The method comprises the steps of separably bonding two discrete jaws to spaced-apart portions of the external surface of the prosthesis to be extracted, coupling the jaws to an extracting tool by at least one flexible element and pulling the tool in a direction to detach the prosthesis frown the at least one tooth. The coupling step can be carried out prior or subsequent to the bonding step, and the flexible element can constitute an endless cable, wire, rope, cord or the like (hereinafter called cable) or a cable of finite length.

The bonding step can comprise separably affixing the jaws to spaced-apart portions of the external surface, preferably to portions which are disposed at least substantially opposite each other, i.e., so that the at least one tooth is located between the jaws upon completion of the bonding step.

The flexible element can constitute a resilient cable which can resemble a yoke and serves to bias the jaws against the adjacent portion of the external surface of the prosthesis.

The bonding step can include applying layers of a rapidly setting adhesive between the jaws and the respective portions of the external surface of the prosthesis. The adhesive can be selected in such a way that it sets in response to the exposure to radiation. The jaws then preferably consist of a material which is permeable to such radiation. The bonding step then further comprises directing radiation against the layers of adhesive through the respective jaws. The radiation can be light, e.g., ultraviolet light. The directing step can include confining the radiation to propagation through an optical conductor.

The adhesive is preferably soluble in a suitable solvent, and the method then further comprises the step of dissolving the adhesive upon detachment of the prosthesis from the at least one tooth.

Another feature of the invention resides in the provision of an implement or apparatus or kit for nondestructive extraction of a dental prosthesis of the type affixed to at least one tooth of a patient. The improved implement comprises two discrete jaws which are bondable to spaced-apart portions of the external surface of a prosthesis to be extracted, an extracting hook (e.g., a tool which can be pulled by hand), and elongated flexible coupling means for separably connecting the jaws with the tool. The coupling means comprises at least one flexible element in the form of a cable, cord, wire, string or the like (hereinafter called cable), and the jaws include portions, for example portions which are connected or connectable to spaced-apart portions of the cable (e.g., to the end portions of a cable having a finite length). The extracting tool can comprise a follower which is movable longitudinally of the coupling means.

The jaws can be shaped in such a way that each thereof has a side confronting one of two spaced-apart portions of the external surface of the prosthesis to be extracted. The outlines of such sides of the two jaws preferably conform, at least substantially, to the outlines of the respective portions of the external surface of the prosthesis. In other words, those sides which are temporarily bonded to the prosthesis have outlines which are at least substantially complementary to the outlines of the adjacent portions of the external surface of the prosthesis. The arrangement can be such that the jaws are deformable (e.g., by resorting to pliers) in order to alter their original configuration to the extent which is necessary to ensure that the outline of one side of each of the thus treated jaws conforms, at least substantially, to the outline of the adjacent portion of the external surface of the prosthesis which is to be extracted from a patient's mouth for the purpose of replacement, inspection, cleaning or repair.

Each jaw can have a substantially cylindrical shape or a substantially conical shape. Those sides of the jaws which face away from the adjacent portions of the external surface of a prosthesis to be extracted can be provided with circular or partly circular (e.g., arcuate) grooves for portions of the cable. If the jaws are relatively thin discs, that side of each jaw which faces away from the adjacent portion of the external surface of a prosthesis can be provided with a projection (e.g., in the form of a hook or stud having an enlarged portion or head spaced apart from the nearer side of the respective jaw) which can serve for coupling the jaw to a portion of the cable. The cable can be an endless cable; alternatively, the cable can have a finite length and its end portions can constitute eyelets serving to receive portions of studs, hooks or otherwise configurated projections at the outer sides of the jaws. The cable can resemble or constitute a resilient yoke having two end portions arranged to bias the jaws against the adjacent portions of the external surface of a prosthesis; this is of advantage while the jaws are being bonded to the adjacent portions of the external surface of a prosthesis.

The jaws can be made of a radiation-transmitting material (e.g., a plastic substance), and such jaws are bondable to the respective portions of the external surface of a prosthesis by an adhesive which sets in response to the exposure to suitable radiation through the respective jaw. If the radiation is light (e.g., ultraviolet light), the material of the jaws is permeable to light. Such light can be caused to pass through an optical conductor, one end of which is placed against or adjacent to the outer side of a jaw, the other side of which is to be bonded to a portion of the external surface of a prosthesis by an adhesive which is polymerizable in response to the exposure to radiation.

The novel features which are considered as characteristic of the invention are set forth in particular in the appended claims. The improved implement or kit itself, however, both as to its construction and the mode of utilizing the same, together with additional features and advantages thereof will be best understood upon perusal for the following detailed description of certain presently preferred specific embodiments with reference to the accompanying drawings.

DESCRIPTION OF PREFERRED EMBODIMENTS

Figure 1:
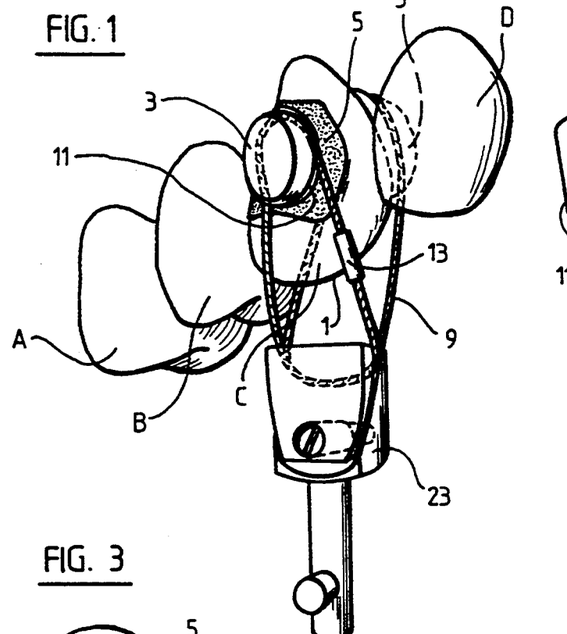
FIG. 1 is a perspective view of four adjoining teeth in the upper jaw of a patient, one of the teeth being surrounded by a crown-shaped prosthesis which is separably bonded to an implement embodying one form of the present invention.

FIG. 1 illustrates four adjoining teeth A, B, C, D in the upper jaw of a patient (with the gums and the jaw omitted). The tooth C is confined in a dental prosthesis in the form of a single crown 1 which is made of metal, ceramic or metal-ceramic compound. A suitable cement (not specifically shown) serves to bond the internal surface of the crown 1 to the external surface of the tooth C. As used herein, the term "tooth" is intended to embrace an intact tooth as well as a stub which has been configured for the purpose of receiving a crown.

The improved implement comprises two crown-engaging components 3 (hereinafter called jaws for short) one of which is bonded to the outer side and the other of which is bonded to the inner side of the crown. Thus, the jaws 3 are bonded to two spaced-apart portions of the external surface of the crown 1, and such spaced-apart portions are disposed opposite each other (with the tooth C between them). An adhesive substance 5 which bonds the jaws 3 to the adjacent portions of the external surface of the crown 1 is a thermally polymerizable or photopolymerizable bonding agent which is capable of quick curing in response to the exposure to heat, light or another energy source. It is presently preferred to employ a bonding agent which is polymerizable in response to the exposure to light, e.g., ultraviolet light. Furthermore, it is desirable to select a bonding agent which can withstand pronounced and abrupt stresses or loads. Still further, it is desirable to select a bonding agent which can be completely separated from the external surface of the crown and preferably from the adjacent sides of the jaws 3 in response to contact with a suitable solvent. For example, the adhesive layers 5 can consist of a rapidly polymerizable material which sets in response to the exposure to ultraviolet light (preferably within one or more seconds or even a fraction of a second) and which can be acted upon by a solvent upon completion of the extracting step so as to be completely removed from the exposed surface of the crown. This renders it possible to reinstall the crown in the mouth of a patient. It is also desirable to select an adhesive material which can be completely separated from the jaws 3 so that the jaws can be reused for extraction of other crowns or larger dental prostheses.

It is desirable to select the configuration of the jaws 3 in such a way that their inner sides 7 (namely those sides which are to be bonded to adjacent portions of the external surface of a crown 1) have an outline at least substantially complementary to the outline of the adjacent portion of the external surface of the crown. This ensures that the adhesive layer 5 has a constant or nearly constant thickness and can be caused to set in a highly predictable manner. Furthermore, the application of an adhesive layer 5 having a uniform thickness ensures predictable removal of all traces of such layer from the external surface of the crown 1 upon completion of the extracting step. Still further, the utilization of jaws having inner sides 7 with outlines conforming to the outlines of adjacent portions of the external surface of the crown renders it possible to ensure more predictable application of adhesive layers 5, i.e., to ensure that the polymerized layers 5 will be maintained in large-area contact with the adjacent sides 7 as well as with the adjacent portions of the external surface of the crown 1. Such large-area contact is desirable because the jaws 3 are even less likely to move relative to or to be separated from the crown 1 prior to separation of the crown from the tooth C.

Figure 11:
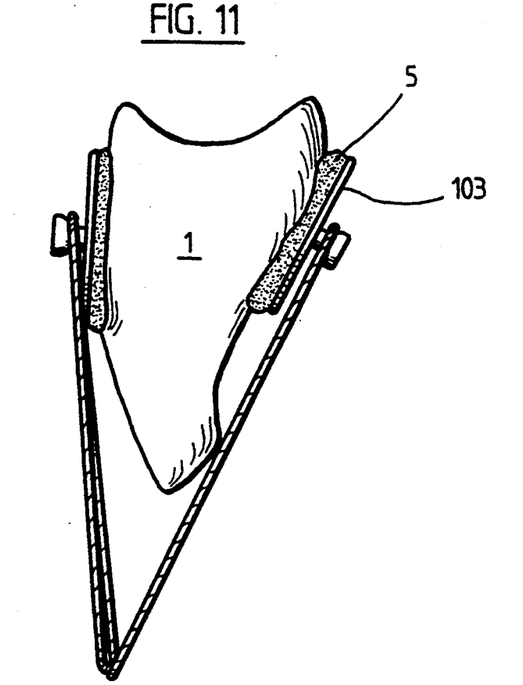
FIG. 11 is a view similar to that of FIG. 9 but showing an implement with two disc-shaped jaws.

The jaws 3 can constitute relatively short cylinders (reference may be made, for example, to FIG. 9), relatively short conical frusta (FIG. 1), relatively thin and readily deformable discs (FIG. 11) or combinations of such and/or other configurations. FIGS. 4 to 7 show relatively thin disc-shaped jaws 103 which are deformed (e.g., by pliers) so as to conform to the outlines of adjacent portions of the external surface of the crown 101.

Figure 2:
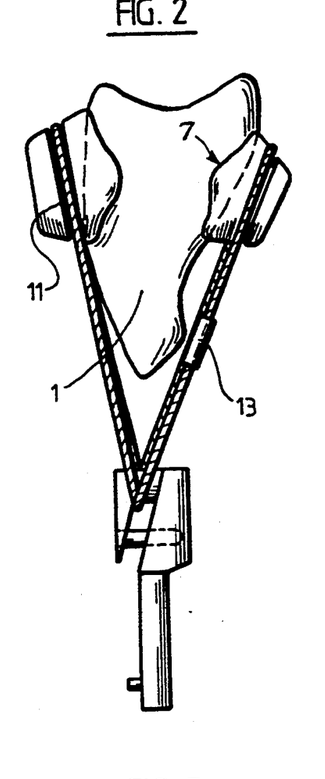
FIG. 2 is an enlarged side elevational view of the prosthesis of FIG. 1 and of the implement which is ready to facilitate separation of the prosthesis from the respective tooth.
Figure 3:
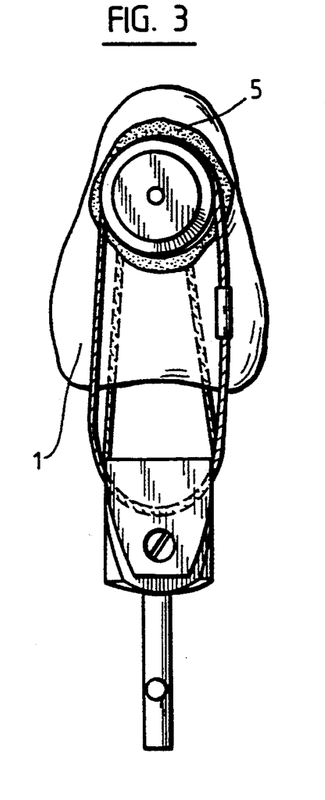
FIG. 3 is a front elevational view of the structure which is shown in FIG. 2.

The improved implement further comprises means for releasably coupling the jaws 3 or 103 with a follower 23 forming part of a tool which is manipulated by a dentist to pull the crown 1 or 101 off the respective tooth (such as the tooth C in FIG. 1). The coupling means in the implement of FIGS. 1 to 3 is an endless flexible element 9 (hereinafter called cable for short) which is looped around outwardly extending projections of the jaws 3 and a hook-shaped portion of the follower 23. The external projections of the jaws 3 have circumferentially extending grooves 11 for the adjacent looped portions of the cable 9. The latter can constitute a finite length of wire, cord or the like having its end portions connected to each other by a suitable (e.g. tubular) connector 13. The follower 23 can be pulled downwardly (note the arrow F in FIG. 9) by a device which is or can be similar to or identical with that shown in FIG. 3 of U.S. Pat. No. 5,197,877 to Andrew. The disclosure of this patent is incorporated herein by reference.

Figures 8, 9, 10:
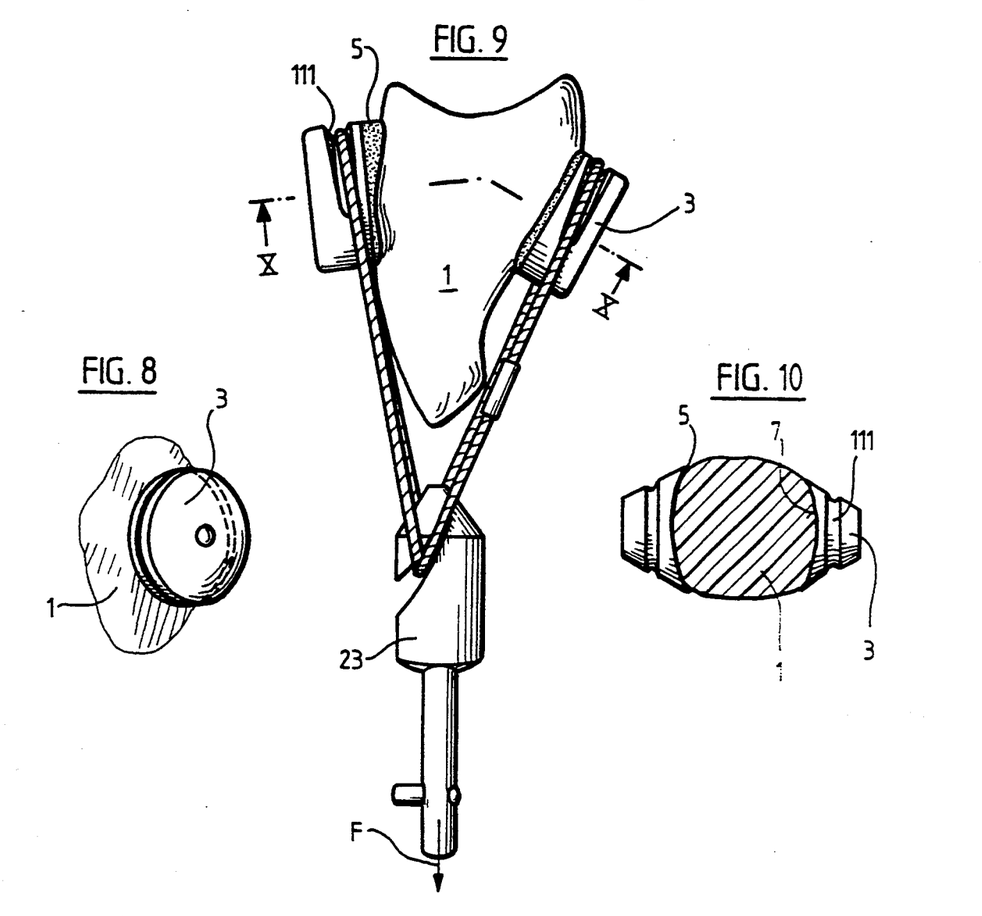
FIG. 8 is a perspective view of a single jaw and of a grooved projection at the outer side of the jaw.
FIG. 9 is a view similar to that of FIG. 2 but showing a modified implement employing two cylindrical jaws.
FIG. 10 is a sectional view substantially as seen in the direction of arrows from the line X—X in FIG. 9.

The outwardly extending projections of the jaws 3 or 103 can be provided with circumferentially complete grooves 11 (as actually shown in FIGS. 1–3) or with arcuate grooves 111 of finite length (FIGS. 9 and 10).

The relatively thin and deformable disc-shaped jaws 103 of the type shown in FIGS. 4–7 can be furnished in deformed condition by the manufacturer, or they are deformed by a dentist in order to conform their inner sides to the outlines of the adjacent portions of a crown 1 or 101 which is to be detached from a tooth. It is also possible to furnish the jaws 103 to a dentist in partly deformed condition, and the dentist thereupon alters the configuration of such jaws in order to ensure that the thus deformed jaws and the adjacent portions of the external surface of a crown 1 or 101 will define clearances of constant width for adhesive layers 5 or 105 having a constant or nearly constant thickness.

Figure 4:
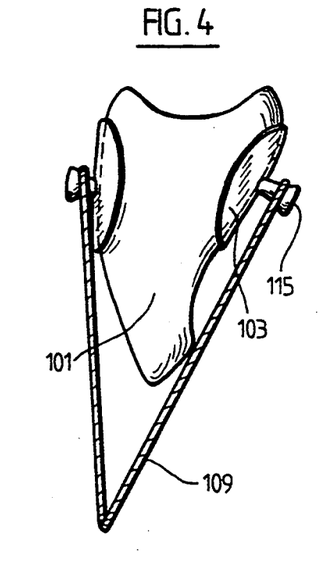
FIG. 4 is a side elevational view similar to that of FIG. 2 but showing a modified implement which is ready to permit extraction of a crown-shaped prosthesis.
Figure 5:
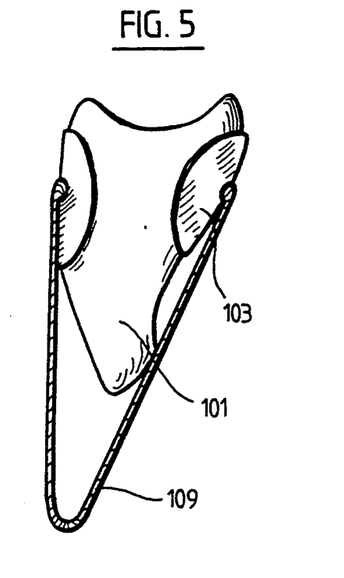
FIG. 5 is a side elevational view of a third implement constituting a modification of the implement of FIG. 4.
Figure 6:
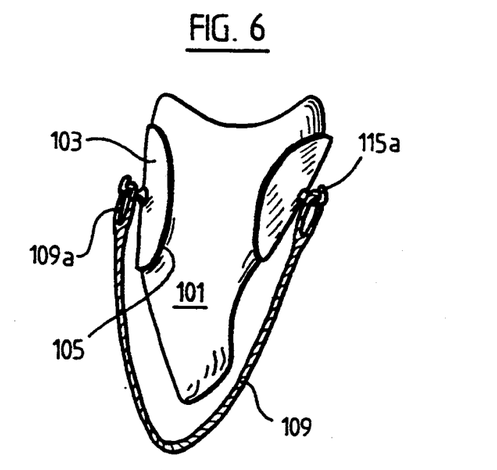
FIG. 6 is a side elevational view of an additional implement which is separably bonded to a crown-shaped prosthesis.

FIG. 4 shows two arcuate disc-shaped jaws 103 having outer sides provided with outwardly extending projections 115 in the form of pins or studs having enlarged free end portions or heads. The projections 115 can extend through eyelets disposed at the ends of a cable 109 and each defining a loop located between the eyelets and serving to engage a hooked portion of a follower 23 (not shown in FIG. 4). FIG. 5 shows jaws 103 which are welded, soldered or otherwise more or less permanently affixed to the adjacent end portions of a cable 109 which corresponds to the similarly referenced cable of FIG. 4 except that its end portions need not constitute or include eyelets. Distinct eyelets 109a are provided at the ends of a cable 109 which is shown in FIG. 6. Each eyelet 109a receives a portion of a hook-shaped projection 115a at the outer side of the respective substantially disc-shaped jaw 103.

Figure 7:
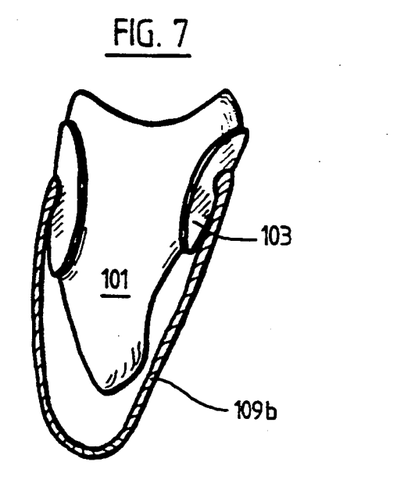
FIG. 7 is a side elevational view of a prosthesis and a further implement.

FIG. 7 shows a resilient yoke-like cable 109b having end portions welded or soldered to the external surfaces of the respective jaws 103. An advantage of the yoke-like resilient cable 109b of FIG. 7 is that it can bias the jaws 103 against the adjacent portions of the external surface of a crown 101 during setting of an adhesive layer between each jaw and the crown. This reduces the likelihood of displacement of the jaws and crown relative to each other during polymerization of the material of the adhesive layers. The cable 109b of FIG. 7 can constitute a length of wire which is resilient and can bias the jaws 103 with a requisite force. The end portions of the yoke 109b can be welded or soldered to the respective jaws 103 in order to ensure that the yoke 109b can extract a crown 101 which has been bonded to the jaws 103 of FIG. 7.

The jaws 3 or 103 can be made of a plastic material (such as polycarbonate), a metallic material or any other suitable material. Jaws of polycarbonate are preferred if the adhesive layers 5 are polymerizable in response to the exposure to ultraviolet light. As a rule, the time which is required for polymerization is less than one minute. This is desirable and advantageous if the adhesive layers 5 are to be exposed to ultraviolet light, i.e, it requires only short-lasting exposure of a patient's mouth to ultraviolet radiation.

If the adhesive layers 5 are made of a substance (e.g., a compound consisting of two different materials) which is not hardenable in response to exposure to ultraviolet light, or if the adhesive layers 5 do not consist of an immediately setting material (e.g., a material which sets within one second or less), it is necessary to press the jaws 3 or 103 against the adjacent portions of a crown 1 or 101 for a longer interval of time. It is then desirable to resort to the embodiment of FIG. 7 wherein the yoke 109b can bias the jaws 103 against the adjacent portions of crown 101 for any desired period of time.

Figure 12:
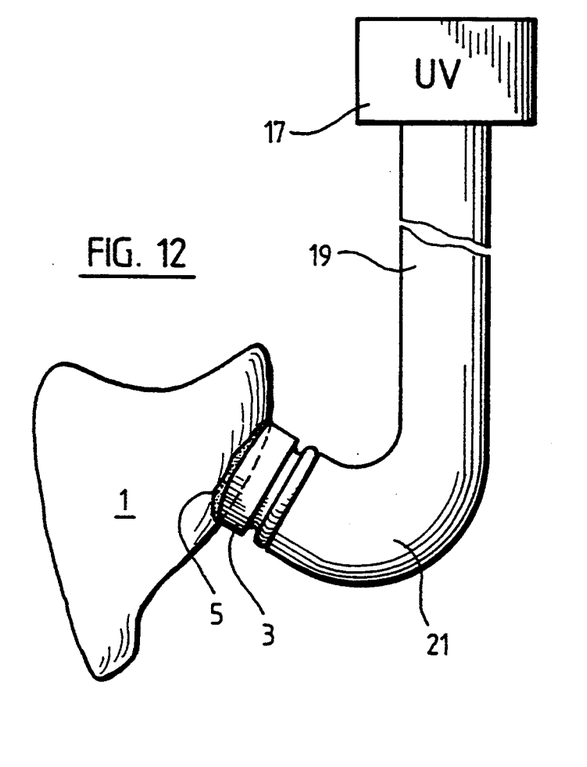
FIG. 12 illustrates an implement which is used to expedite the bonding of a jaw to a selected portion of the external surface of a prosthesis.

FIG. 12 illustrates one presently preferred mode of exposing a photopolymerizable adhesive substance 5 to the polymerizing action of ultraviolet radiation through the respective jaws 3. The reference character 17 denotes a source of ultraviolet light, and the beam of radiation issuing from such source propagates itself through a photoconductor 19 having a suitably bent end portion 21 engageable with the exposed side of a jaw 3. The jaws 3 are made of polycarbonate or another material which is permeable to ultraviolet light. The orientation of the end portion 21 of the conductor 19 is preferably such that the ultraviolet rays issuing from the source 17 impinge upon the expose side of a jaw 3 at least substantially at right angles to the plane of such outer side. This ensures predictable penetration of ultraviolet light through the layer 5 of photopolymerizable material and predictable as well as rapid polymerization to thus establish a strong but readily soluble bond between a jaw 3 and the adjacent portion of the crown 1. The conductor 19 can comprise or can consist or constitute the discharge end of a bundle of optical fibers because such bundle can be readily manipulated by a dentist to ensure rapid and predictable bonding of the jaws 3 to selected portions of the external surface of the crown 1 or another dental prosthesis. Moreover, the utilization of an elongated bundle of optical light-transmitting fibers renders it possible to install or position the source 17 at a desired distance from the patient.

The manner of extracting a crown 1 or 101 from a tooth (such as the tooth C shown in FIG. 1) is as follows:

A dentist or a technician couples the free ends of a cable 9 of the type shown in FIGS. 1–3 to each other by utilizing the sleeve-like connector 13 in order to obtain an endless flexible coupling element. The ends of the cable 9 can be welded or otherwise connected to each other, i.e., the sleeve 13 constitutes but one of numerous devices which can be used to form the endless cable 9 of FIGS. 1–3. Spaced-apart portions of the endless cable 9 are inserted into the grooves 11 of projections at the outer sides of the jaws 3, and additional portions of the cable 9 are engaged by the hook-shaped portion of the follower 23 so that the latter can move back and forth along the cable 9 between the jaws 3. The follower 23 is separably or otherwise secured to one end portion of rod-shaped guide of the type shown in FIG. 3 of U.S. Pat. No. 5,197,877 to Andrew or another suitable tool. Tools of the type shown in FIG. 3 of the patent to Andrew are available to and are used by dentists all over the world. For example, the tool shown in FIG. 3 of the patent to Andrew can be replaced by a simple hook, which can be used to exert a pull upon the jaws 3 of FIGS. 1–3 while such jaws are bonded to the crown 1. An advantage of the tool which is shown in FIG. 3 of the patent to Andrew is that its hammer can be used to apply a pulling force of desired magnitude at desired intervals so as to loosen the crown 1 and disengage it from the tooth C. A set of simple hooks which can be used in lieu of the aforediscussed tool disclosed in the patent to Andrew and such hooks are also available to dentists all over the world. It is further clear that the follower 23 of a pulling tool can be attached to a selected portion of the cable 9 or another cable (such as the cable 109 of FIG. 6) before the cable is attached to the jaws 3 of FIGS. 1–3 or to the jaws 103 of FIG. 6. Analogously, the eyelets (such as 109a) at the ends of the cable 109 in FIG. 6 can be coupled to the respective jaws 103 prior or subsequent to attachment of such cable to a follower 23. The situation is even simpler if the dentist employs an implement of the type shown in FIGS. 5 or 7, i.e., an implement wherein the ends of the cable are inseparably affixed to the outer sides of the respective jaws. At any rate, the sequence in which (a) the jaws 3 or 103 are bonded to a crown 1 or 101 and (b) the cable 9 or 109 is attached to a follower is up to the dentist.

Since the follower 23 is free to travel along the flexible cable, a pull upon the tool which includes or carries the follower 23 or an analogous follower is properly distributed between the two jaws 3 or 103. Thus, and referring to FIG. 9, a pull upon the follower 23 in the direction of the arrow F is transmitted to both jaws 3 and hence to two spaced apart portions of the crown 1 with the result that the detachment of the crown from a tooth can be completed in response to the exertion of a relatively small force and that the crown is unlikely to be deformed and/or otherwise damaged during separation from a tooth. The distribution of pulling force which is applied in the direction of arrow F is uniform even if such direction is not exactly normal to a line connecting the centers of the two jaws 3. Furthermore, such distribution of pulling force is highly satisfactory even if the two jaws 3 are not bonded to two portions of the external surface of a crown which are disposed exactly opposite each other, either due to inaccurate bonding of the one or the other jaw or due to the outline of the crown 1.

The situation (i.e., adequate distribution of pull tooth jaws) is analogous if the follower 23 or a similar or analogous follower is coupled with a cable of the type shown in FIGS. 4–7 and 11.

Once the crown 1 or 101 is detached from the tooth, it is placed into a bath containing a solvent which dissolves the polymerized adhesive layers 5 so that the crown is not only separated from the jaws 3 or 103 but is also undamaged and ready for renewed use or repair work of a nature not necessitated by extraction of the crown in the aforedescribed manner. The detached jaws 3 or 103 are also ready for renewed use.

The improved implement can be utilized in combination with one or more additional implements to extract more complex dental prostheses, e.g., prostheses containing at least one pair of crowns which are coupled to each other by a bridge.

It has been found that the improved implement and the novel method of utilizing such implement for extraction of dental prostheses not only ensure that the prosthesis is not damaged during extraction but that they also reduce the likelihood of damage to the cement which was used to bond the prosthesis to one or more teeth. One of the important reasons for the ability of the improved implement to facilitate the extraction of dental prostheses is that the tool including the follower 23 or an analogous tool is capable of properly distributing the pull to both jaws 3 or 103 even if the jaws are not affixed to a crown in optimum positions, namely exactly opposite each other. This simplifies the task of the dentist because she or he need not be concerned with highly accurate bonding of the jaws 3 or 103 to a crown in optimum positions with reference to each other.

The improved implement can be furnished with several pairs of jaws so that the dentist can select a pair which is best suited for attachment to a particular crown. As already mentioned above, the jaws 3 or 103 can be furnished in the form of concavo-convex discs or similar configurations, i.e., they can be provided with sides which are expected to conform to portions of external surfaces of a large number of crowns. If additional shaping of the jaws is necessary, such work can be carried out by the dentist based on the actual outline of those portions of the external surface of a crown which are to be connected to the jaws. It is normally desired to shape the jaws 3, 103 or analogous jaws in a manner to ensure that relatively thin layers of adhesive 5 will suffice to establish a reliable connection between the jaws and selected portions of a crown. This not only ensures rapid polymerization of thin adhesive layers in response to exposure to radiation (or heat or both) but also ensures rapid dissolution of adhesive 5 upon extraction of a prosthesis from a patient's mouth.

For example, the adhesive layers 5 can consist of a modified acrylate (such as "PENLOCK GTI" (Trademark) distributed by Panacol, Zürich, Switzerland), and the solvent can be acetone.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of any contribution to the art and, therefore, such adaptations should and are intended to be comprehended within the meaning and range of equivalence of the appended claims.

We claim:

1. An implement for nondestructive extraction of a dental prosthesis of the type affixed to at least one tooth and having an external surface, comprising two discrete jaws bondable to spaced-apart portions of the external surface of a prosthesis; an extracting tool; and elongated flexible coupling means for separably connecting said jaws with said tool, said extracting tool comprising a follower movable longitudinally of said coupling means.

2. The implement of claim 1, wherein said coupling means comprises at least one cable having first and second ends and said jaws include portions connectable with the ends of said cable.

3. The implement of claim 1 for extraction of a dental prosthesis having an external surface including two spaced-apart portions having first outlines, wherein said jaws have sides confronting the respective portions of the external surface and having second outlines at least substantially complementary to the confronting portions of the external surface.

4. The implement of claim 1 for extraction of a dental prosthesis having an external surface including two spaced-apart portions having first outlines, wherein said jaws are deformable to at least substantially conform to the outlines of the respective portions of the external surface.

5. A method of nondestructively extracting a dental prosthesis of the type affixed to at least one tooth and having an external surface, comprising the steps of separably bonding two discrete jaws to spaced-apart portions of the external surface of the prosthesis; coupling the jaws to an extracting tool by at least one flexible element; and pulling the tool in a direction to detach the prosthesis from the at least one tooth.

6. The method of claim 5, wherein said bonding step comprises separably affixing the jaws to spaced-apart portions of the external surface which are disposed at least substantially opposite each other with the at least one tooth between the affixed jaws.

7. The method of claim 5, wherein said coupling step includes connecting the tool with the discrete jaws by at least one resilient cable.

8. The method of claim 5, wherein said bonding step includes applying layers of a rapidly setting adhesive between the jaws and the respective portions of the external surface of the prosthesis.

9. The method of claim 8, wherein said adhesive sets in response to the exposure to radiation and said jaws consist of a material which is permeable to such radiation, said bonding step further comprising directing radiation against the layers of adhesive through the respective jaws.

10. The method of claim 9, wherein said radiation is light.

11. The method of claim 9, wherein said directing step comprises confining the radiation to propagation through an optical conductor.

12. The method of claim 8, wherein the adhesive is soluble in a solvent and further comprising the step of dissolving the adhesive upon detachment of the prosthesis from the at least one tooth.

13. An implement for nondestructive extraction of a dental prosthesis of the type affixed to at least one tooth and having an external surface, comprising two discrete jaws bondable to spaced-apart portions of the external surface of a prosthesis; an extracting tool; and elongated flexible coupling means for separably connecting said jaws with said tool, said coupling means comprising at least one cable having first and second ends and said jaws including portions connectable with the ends of said cable.

14. The implement of claim 13, wherein said extracting tool comprises a follower movable longitudinally of said coupling means.

15. An implement for nondestructive extraction of a dental prosthesis of the type affixed to at least one tooth and having an external surface, comprising two discrete jaws bondable to spaced-apart portions of the external surface of a prosthesis, each of said jaws having a substantially cylindrical shape; an extracting tool; and elongated flexible coupling means for separably connecting said jaws with said tool.

16. An implement for nondestructive extraction of a dental prosthesis of the type affixed to at least one tooth and having an external surface, comprising two discrete jaws bondable to spaced-apart portions of the external surface of a prosthesis, each of said jaws having a substantially conical shape; an extracting tool; and elongated flexible coupling means for separably connecting said jaws with said tool.

17. An implement for nondestructive extraction of a dental prosthesis of the type affixed to at least one tooth and having an external surface, comprising two discrete jaws bondable to spaced-apart portions of the external surface of a prosthesis; an extracting tool; and elongated flexible coupling means for separably connecting said jaws with said tool, each of said jaws having a first side confronting the respective portion of the external surface and a second side having a groove for a portion of said flexible coupling means.

18. An implement for nondestructive extraction of a dental prosthesis of the type affixed to at least one tooth and having an external surface, comprising two discrete jaws bondable to spaced-apart portions of the external surface of a prosthesis; an extracting tool; and elongated flexible coupling means for separably connecting said jaws with said tool, each of said jaws including a disc having a first side facing the respective portion of the external surface and a second side provided with a projection engageable by a portion of said flexible coupling means.

19. The implement of claim 18, wherein said projections are studs.

20. The implement of claim 18, wherein said projections are hooks.

21. An implement for nondestructive extraction of a dental prosthesis of the type affixed to at least one tooth and having an external surface, comprising two discrete jaws bondable to spaced-apart portions of the external surface of a prosthesis; an extracting tool; and elongated flexible coupling means for separably connecting said jaws with said tool, said coupling means including an endless cable.

22. An implement for nondestructive extraction of a dental prosthesis of the type affixed to at least one tooth and having an external surface, comprising two discrete jaws bondable to spaced-apart portions of the external surface of a prosthesis; an extracting tool; and elongated flexible coupling means for separably connecting said jaws with said tool, said flexible coupling means having first and second ends constituting eyelets connectable to projections provided on said jaws.

23. An implement for nondestructive extraction of a dental prosthesis of the type affixed to at least one tooth and having an external surface, comprising two discrete jaws bondable to spaced-apart portions of the external surface of a prosthesis; an extracting tool; and elongated flexible coupling means for separably connecting said jaws with said tool, said coupling means including a resilient yoke having end portions arranged to bias said jaws against the respective portions of the external surface of a prosthesis.

24. An implement for nondestructive extraction of a dental prosthesis of the type affixed to at least one tooth and having an external surface, comprising two discrete jaws bondable to spaced-apart portions of the external surface of a prosthesis, said jaws consisting of a radiation-transmitting material and being bondable to the respective portions of the external surface of a prosthesis by adhesive which sets in response to exposure to radiation through the respective jaws; an extracting tool; and elongated flexible coupling means for separably connecting said jaws with said tool.

25. The implement of claim 24, wherein said jaws consist of a plastic material which is permeable to light.

26. An implement for nondestructive extraction of a dental prosthesis of the type affixed to at least one tooth and having an external surface, comprising two discrete jaws bondable to spaced-apart portions of the external surface of a prosthesis; an extracting tool; and elongated flexible coupling means for separably connecting said jaws with said tool, said coupling means including an endless cable and said tool including a follower which is slidable along said cable.

27. An implement for nondestructive extraction of a dental prosthesis of the type affixed to at least one tooth and having an external surface, comprising two discrete jaws bondable to spaced-apart portions of the external surface of a prosthesis; an extracting tool; and elongated flexible coupling means for separably connecting said jaws with said tool, said coupling means including a cable having first and second end portions each connectable to one of said jaws and said tool comprising a follower which is slidable along said cable intermediate said end portions thereof. pg,28

* * * * *